(12) United States Patent
Bowman et al.

(10) Patent No.: US 8,567,397 B2
(45) Date of Patent: Oct. 29, 2013

(54) METHODS FOR BATTERY POWER MANAGEMENT OF POSITIVE AIRWAY PRESSURE APPARATUS

(75) Inventors: Bruce R. Bowman, Eden Prairie, MN (US); Joseph A. Baser, Lino Lakes, MN (US); Steven S. Bordewick, Shoreview, MN (US); John R. Hanson, Falcon Heights, MN (US)

(73) Assignee: Somnetics Global Pte. Ltd., Singapore (SG)

( * ) Notice: Subject to any disclaimer, the term of this patent is extended or adjusted under 35 U.S.C. 154(b) by 917 days.

(21) Appl. No.: 12/496,967

(22) Filed: Jul. 2, 2009

(65) Prior Publication Data

US 2010/0065054 A1  Mar. 18, 2010

Related U.S. Application Data

(60) Provisional application No. 61/133,862, filed on Jul. 2, 2008.

(51) Int. Cl.
*A61M 16/00* (2006.01)
*H02J 7/00* (2006.01)

(52) U.S. Cl.
USPC ..................................... 128/204.21; 320/132

(58) Field of Classification Search
USPC ................. 320/132; 455/574, 127.5, 343.5; 128/204.21, 200.24, 204.18
See application file for complete search history.

(56) References Cited

U.S. PATENT DOCUMENTS

| | | | |
|---|---|---|---|
| 4,493,614 A | 1/1985 | Chu et al. | |
| 4,957,107 A | 9/1990 | Sipin | |
| 5,237,987 A | 8/1993 | Anderson et al. | |
| 7,134,029 B2 * | 11/2006 | Hepner et al. | 713/300 |
| 7,363,519 B2 | 4/2008 | Liebenow | |
| 8,001,400 B2 * | 8/2011 | Fadell | 713/320 |
| 2006/0143483 A1 * | 6/2006 | Liebenow | 713/300 |
| 2006/0213516 A1 | 9/2006 | Hoffman | |
| 2006/0231097 A1 * | 10/2006 | Dougherty et al. | 128/204.18 |
| 2007/0150019 A1 * | 6/2007 | Youker et al. | 607/29 |
| 2007/0182376 A1 * | 8/2007 | Doyle | 320/132 |
| 2008/0099017 A1 | 5/2008 | Bordewick et al. | |
| 2008/0149101 A1 | 6/2008 | Becker et al. | |
| 2011/0162647 A1 * | 7/2011 | Huby et al. | 128/203.14 |

FOREIGN PATENT DOCUMENTS

| | | |
|---|---|---|
| WO | WO 2004/112873 A1 | 12/2004 |
| WO | WO 2006/050384 A2 | 5/2006 |

OTHER PUBLICATIONS

Communication pursuant to Article 94(3) EPC dated Jun. 12, 2012 for European Application No. 09 774 513.7-2320; 4 pgs.
International Preliminary Report on Patentability and Written Opinion dated Jan. 5, 2011 for PCT/US2009/049526; 8 pgs.
International Search Report dated Sep. 29, 2009 for PCT/US2009/049526; 5 pgs.
Moran, "CPAP outside the box," *HME News*, May 2006; 2 pgs.
U.S. Appl. No. 61/133,862, filed Jul. 2, 2008, Bowman et al.
Communication pursuant to Article 94(3) EPC dated Apr. 5, 2013 for European Application No. 09 774 513.7—1662; 5 pgs.

\* cited by examiner

*Primary Examiner* — Lynne Anderson
*Assistant Examiner* — Bradley Philips
(74) *Attorney, Agent, or Firm* — Mueting, Raasch & Gebhardt, P.A.

(57) ABSTRACT

Methods relating to the power management of positive airway pressure apparatus using a battery are disclosed herein. The methods, in various aspects, are adapted to prolong the delivery of a positive airway pressurized therapy when the positive airway pressure apparatus is operated under battery power.

8 Claims, 7 Drawing Sheets

METHODS FOR BATTERY POWER MANAGEMENT OF POSITIVE AIRWAY PRESSURE APPARATUS

CROSS-REFERENCE TO RELATED APPLICATIONS

The present application claims benefit and priority from a U.S. Provisional Patent Application having Ser. No. 61/133,862 filed on Jul. 2, 2008 the disclosure of which is hereby incorporated by reference in its entirety.

BACKGROUND OF THE INVENTION

1. Field of the Invention

This disclosure relates to positive pressurized respiratory therapy and, more particularly, to apparatus and methods for managing battery discharge during the delivery of positive pressure respiratory therapies.

2. Description of the Related Art

Positive airway pressure therapy devices are used to deliver positive pressure therapy for the treatment of obstructive sleep apnea, chronic pulmonary obstruction, and snoring. A power source is provided to operate the positive airway pressure therapy device. The power source may be mains electric including commercial electric utilities as well as a generator such as a generator attached to a vehicle motor. A battery may also serve as the power source. The battery is a useful power source when mains electric is not convenient or is not available, and the battery may also serve as a backup power source in the event of failure of the mains electric.

While under battery power, various components included in the positive airway pressure therapy device may continue to draw power and otherwise operate as though the positive airway pressure therapy device is connected to mains electric until the battery charge of the battery is more-or-less exhausted, at which time the positive airway pressure therapy device shuts down. For example, this shut-down may occur while the user is sleeping, so that the user does not receive positive pressure therapy throughout the entire sleeping period. Accordingly, a need exists for methods that prolong the delivery of positive pressure therapy by the positive airway pressure therapy device under battery power.

SUMMARY

Methods disclosed herein may resolve one or more of the needs and shortcomings discussed above and will provide additional improvements and advantages as will be recognized by those of ordinary skill in the art upon review of the present disclosure.

Methods for delivering a positive pressure therapy to a user with a positive airway pressure apparatus are disclosed herein, In various aspects, the methods include powering a positive airway pressure therapy apparatus using a battery, determining a desired therapy duration time over which a positive pressure therapy is expected to be delivered to a user by the positive airway pressure therapy apparatus, and reducing total current drawn from the battery by altering the operation of the positive airway pressure therapy apparatus as necessary to thereby allow the delivery of positive pressure therapy to the user for at least the remaining therapy time.

The methods, in various aspects, include reducing total current drawn from the battery by altering the operation of the positive airway pressure therapy apparatus thereby allowing the delivery of positive pressure therapy to the user for at least the remaining therapy time which includes reducing the level of added humidity of the pressurized air delivered to the user.

The methods, in various aspects, include reducing the current supplied to a heater disposed about a humidifier.

The methods, in various aspects, include reducing a pulse width of the current supplied to the heater. The pulse width of the current supplied to the heater is reduced by steps in various aspects. The desired therapy duration time is set at a fixed value, in various aspects.

The methods, in various aspects, include inputting a desired therapy duration time into the positive airway pressure therapy apparatus, tracking the time that the positive pressure therapy has been delivered to the user, and calculating the remaining therapy time as the desired therapy duration time minus the time that the positive pressure therapy has been delivered to the user. The methods, in various aspects, include determining a desired therapy duration time from the history of use of the positive airway pressure apparatus, tracking the time that the positive pressure therapy has been delivered to the user; and calculating the remaining therapy time as the desired therapy duration time minus the time that the positive pressure therapy has been delivered to the user.

The methods, in various aspects, include determining a total current drawn from a battery by a positive airway pressure therapy apparatus, calculating a remaining battery operational time using the total current and a battery charge of the battery, and altering the total current such that the remaining battery operational time exceeds a remaining therapy time. The desired therapy duration time is set at a fixed value in some aspects. The remaining therapy time is decremented as positive pressure therapy is delivered to the user in some aspects.

The methods, in various aspects, may include inputting a desired therapy duration time into the positive airway pressure apparatus, clocking the time for which the positive pressure therapy has been delivered to the user, and setting the remaining therapy time equal to the desired therapy duration time minus the time for which the positive pressure therapy has been delivered to the user.

The battery charge is set to the maximum battery charge in some aspects. The methods may include detecting the battery charge of the battery, altering the operation of the positive airway pressure apparatus as the battery charge changes in order to deliver positive pressure therapy to the user for the remaining therapy time under battery power, altering the operation of the respiratory therapy apparatus as the remaining therapy time $t_R$ changes in order to deliver positive pressure therapy to the user for the remaining therapy time under battery power. The step of altering the operation of the positive airway pressure therapy apparatus as the battery charge changes in order to deliver positive pressure therapy to the user for the remaining therapy time under battery power which includes altering the current supplied to a heater disposed about a humidifier may be included in the methods. The methods may include detecting the battery charge using a coulomb counter, may include detecting the battery charge through battery impedance measurement, or may include other methods of detecting battery charge.

Other features and advantages of the methods disclosed herein will become apparent from the following detailed description and from the claims.

Figure 1A:
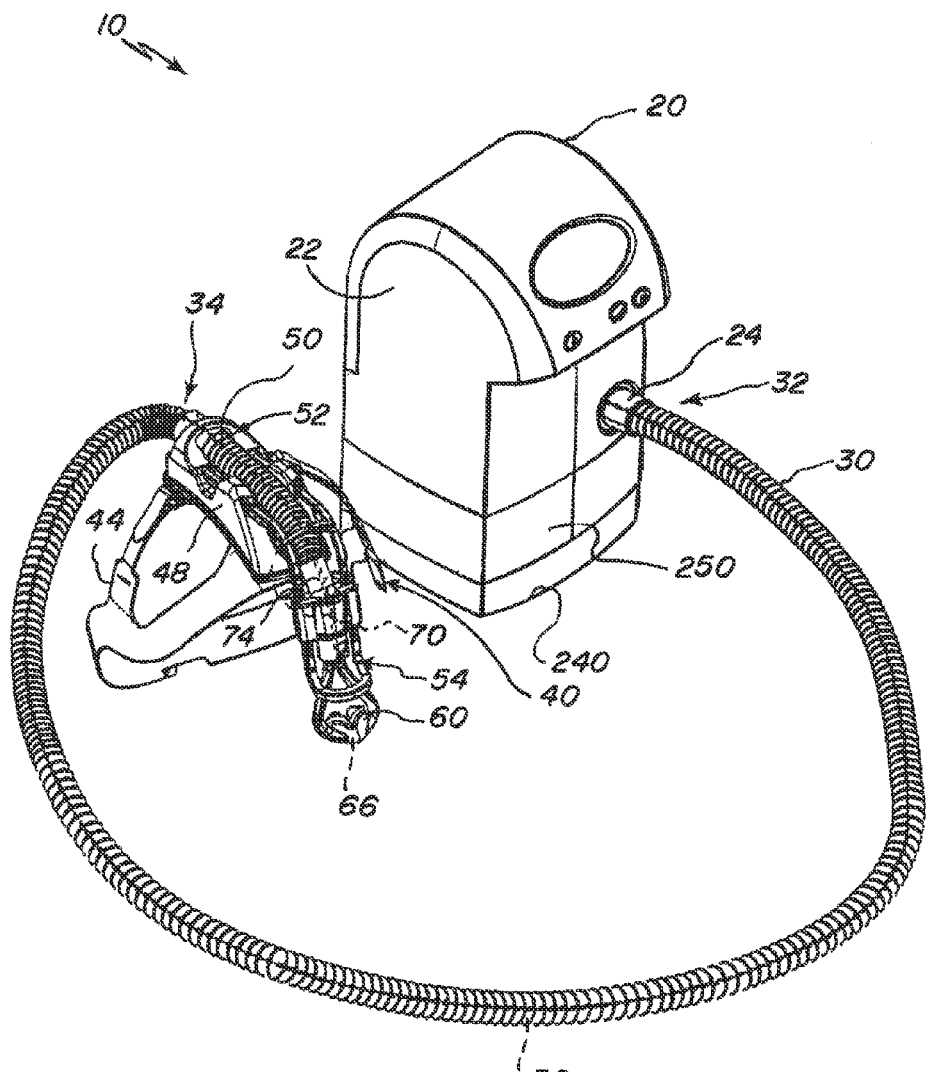
FIG. 1A illustrates by perspective view an implementation of a positive airway pressure apparatus.

All Figures are illustrated for ease of explanation only; the extensions of the Figures with respect to number, position, relationship and dimensions of the parts to form the embodiment will be explained or will be within the ordinary skill of the art after the following description has been read and understood. Further, the exact dimensions and dimensional proportions to conform to specific force, weight, strength, flow and similar requirements will likewise be within the ordinary skill of the art after the following description has been read and understood.

Where used in various Figures of the drawings, the same numerals designate the same or similar parts. Furthermore, when the terms "top," "bottom," "right," "left," "forward," "rear," "first," "second," "inside," "outside," and similar terms are used the terms should be understood to reference only the structure shown in the drawings and is utilized only to facilitate describing the illustrated embodiments.

DETAILED DESCRIPTION OF THE INVENTION

The present inventions provide apparatus and methods for regulation of a battery powering a positive airway pressure apparatus configured to deliver a positive pressure therapy to a user. The positive airway pressure apparatus can include, in various aspects, a user interface in communication with a flow generator, a control unit, and a battery adapted to deliver a positive pressure therapy to a user. The user interface may be configured to be secured relative to the user's head such that a positive pressure therapy may be administered to the user by the positive airway pressure apparatus as the user sleeps. The flow generator is provided as a source of pressurized air, and communicates the pressurized air to the user interface. The user interface is configured to communicate the pressurized air into the airways of a user in order to deliver a positive pressure therapy to the user. A humidifier may be included in the positive airway pressure apparatus in various aspects to humidify the pressurized air delivered to the user.

The control unit regulates the delivery of the pressurized air and otherwise regulates the operation of the positive airway pressure apparatus in order to deliver the positive pressure therapy to the user. An I/O (input/output) interface in communication with the control unit may be provided in various aspects to display information from the control unit with respect to the positive pressure therapy and/or to allow communication of information to the control unit for regulation of the positive pressure therapy. In various aspects, one or more sensors can be disposed throughout the positive airway pressure apparatus to monitor the operation of the positive airway pressure apparatus including the delivery of the positive pressure therapy to the user and/or the user' response to the positive pressure therapy. The sensors may be in communication with the control unit, and the control unit may regulate the delivery of the positive pressure therapy in response to communications from the sensor(s).

The battery is in electrical communication with various portions of the positive airway pressure apparatus to provide electric power to the positive airway pressure apparatus as an alternative to mains electric. When the battery provides electric power to the positive airway pressure apparatus, the control unit is configured to detect the battery charge in the battery and to optimize accordingly the delivery of the positive pressure therapy in order to prolong the delivery of at least some amount of positive pressure therapy to the user. Should mains electric or another outside source of power be reintroduced during operation under the power of a battery, the control unit may revert to standard or non-battery based operation protocols.

The Figures generally illustrate exemplary embodiments of the positive airway pressure apparatus. These illustrated apparatus and methods are not meant to limit the scope of coverage but, instead, to assist in understanding the context of the language used in this specification and in the appended claims. Accordingly, the appended claims may encompass variations that differ from the illustrations.

The positive airway pressure apparatus, in various aspects, are generally configured to provide one or more positive pressure therapies to the user in order to treat, for example, obstructive sleep apnea, chronic pulmonary obstruction, snoring, and/or other related conditions. The positive airway pressure apparatus are generally configured to maintain pressure in a user's airway above atmospheric pressure to maintain the patency of the user's airway. The positive airway pressure apparatus and the positive pressure therapy delivered thereby may include various forms of continuous positive airway pressure (CPAP), bi-level positive airway pressure (BiPAP), auto positive airway pressure (auto-PAP), and/or other related apparatus and positive airway pressure therapies, as would be recognized by those of ordinary skill in the art upon study of this disclosure.

The positive airway pressure apparatus 10 typically includes a user interface 40. The user interface 40 is generally configured to communicate pressurized air communicated from the flow generator 20 into the airways of a user. The pressurized air communicated into airways of the user during the course of the positive pressure therapies includes air as well as other breathable gases. The user interface 40 may be generally configured to be secured to the user and to communicate pressurized air into the airway of the user. The user interface 40 can include a mask 60 configured to be secured over the airways of a user. In certain aspect, the mask 60 may include a cap, one or more support bands 44, or other elements as will be recognized by those of ordinary skill in the art upon study of this disclosure to secure the mask 60 to the user. The user interface 40 may include a mount 48 and various other features such as pads that allow the user interface 40 including the mask 60 to be affixed to the user and that maintain a proper orientation of the user interface 40 including the mask 60 with respect to the user.

The mask 60 portion of the user interface 40 may be configured to communicate the pressurized air generated by the flow generator 20 to the user's airways. In various aspects, the mask 60 may be positioned about the user's nose, the user's mouth, or both the user's nose and mouth in order to provide a generally sealed connection to the user for the delivery of pressurized air for inhalation. A pressure greater than atmospheric pressure may be provided within the sealed connection. Accordingly, portions of the mask 60 may be formed of soft silicone rubber, gel material, or similar material that may provide a seal and that may also be generally comfortable when positioned against the user's skin. In various aspects, the mask 60 may include nasal pieces that fit around the user's nose or around the user's nose and mouth, nostril inserts into the user's nares, or some combination thereof.

The flow generator 20 may include a flow generator housing 22 defining an outlet 24, with the flow generator 20 adapted to deliver pressurized air to the outlet 24. In order to deliver pressurized air to the outlet 24, the flow generator 20 may include one or more of various motors, fans, pumps, turbines, ducts, inlets, conduits, passages, mufflers, and other components, as will be recognized by those of ordinary skill in the art upon review of the present disclosure. In operation, air is drawn into the flow generator 20, compressed by the flow generator, and the resulting pressurized air discharged through the outlet 24.

In some aspects, the flow generator 20 is generally secured about the user's head and the user interface 40 is secured to the outlet of the flow generator 20 so that the flow generator 20 communicates pressurized air into pathways within the user interface 40. In other aspects, the flow generator 20 is positioned generally proximate the user, for example, on a bedside table. A delivery tube 30 may be secured to an outlet 24 of the flow generator 20 to convey pressurized air from the flow generator 20 to the user interface 40. In one aspect, the delivery tube 30 is configured as an elongated flexible tube. The delivery tube 30 may be composed of a lightweight plastic and have a ribbed configuration.

The positive airway pressure apparatus 10, in various aspects, includes a humidifier 250 in communication with the fluid pathways of the positive airway pressure apparatus 10 to introduce moisture into the pressurized air delivered to the user. Electric power may be provided to the humidifier 250 to heat water in order to induce the water to evaporate and/or otherwise facilitate the introduction of moisture into the pressurized air delivered to the user. In some aspects, the humidifier 250 may be generally formed as a heated reservoir about which the pressurized air passes. The humidifier 250, in other aspects could be formed as a vaporizing element heated by current through an electrical resistor upon which water is sprayed to induce the water to vaporize into the pressurized air. In other aspects, the humidifier 250 may include a capillary pump to inject the moisture into the pressurized air, and, in still other aspects, the humidifier 250 may include an ultrasonic element to vaporize water, or the humidifier 250 may include an exchange material that wicks water and through which the pressurized air passes to evaporate water from the exchange material into the pressurized air. Various valves, nozzles, orifices and other fluid control/fluid dispersion devices as well as pumps, heaters, reservoirs, and so forth may be provided in conjunction with the humidifier to manage the introduction of moisture into the pressurized air, as would be recognized by those of ordinary skill in the art upon study of this disclosure. The humidifier 250 may warm the pressurized air delivered to the user in various aspects.

A control unit 26 is included in the positive airway pressure apparatus 10 to regulate the positive airway pressure apparatus 10 including the pressure of the pressurized air delivered to the user in order to deliver one or more positive pressure therapies to the user. The control unit 26 can be positioned about the flow generator housing 22, but may be otherwise positioned or located, including remotely, as will be recognized by those of ordinary skill in the art upon review of the present disclosure. In some aspects, at least portions of the control unit 26 may be located remotely. The control unit 26, in various aspects, includes one or more microprocessors as well as computer readable memory and the attendant circuitry. The control unit 26 may include various communication channels configured so that the control unit 26 may receive signals from and/or output control signals to various components and/or sensors 205 of the positive airway pressure apparatus 10 in order to regulate the positive airway pressure apparatus 10. The communication channels can for example include wires, fibre-optics, as well as various wireless technologies.

The control unit 26 is in communication with the I/O interface 270 in various aspects. The I/O interface 270 may include various screens, switches, dials, indicator lights, and so forth, to communicate information about the operation of the positive airway pressure apparatus 10 from the control unit 26 to the user and/or allow the user to communicate information to the control unit 26 in order to regulate the operation of the positive airway pressure apparatus 10 including the delivery of the positive pressure therapy. For example, the user, via the I/O interface 270, may turn the positive airway pressure apparatus 10 on/off, select the desired therapy duration time $t_o$ of the positive pressure therapy, select therapeutic pressure(s) $p_T$ delivered to the user during the positive pressure therapy, control the initiation of the positive pressure therapy, turn the humidifier 250 on/off, and specify the humidity. The desired therapy duration time $I_D$ is indicative of the time over which the positive pressure therapy may be delivered, and may be selected to generally correspond to the normal resting period of the user. The control unit 26 regulates the positive airway pressure apparatus 10 in response to information communicated to the control unit 26 via the I/O interface 270 in various aspects. In the present embodiments, this information may particularly relate to information relating to the charge Q remaining in the battery 240. For example, the control unit 26 may regulate the flow generator 20 to deliver pressurized air at the therapeutic pressure(s) to the user and otherwise regulate the positive airway pressure apparatus 10 in response to the information communicated via the I/O interface 270.

In various aspects, sensors 205 that detect the physiology of the user and/or the operation of the positive airway pressure apparatus 10 and generate signals indicative thereof are located about the positive airway pressure apparatus 10. The sensors 205, for example, may detect the user's pulse, breathing rate, inhalation, exhalation, and/or noises associated with snoring. The sensors 205 may include Hall Effect transducers and other devices that sense the speed and/or location of various mechanical components of the positive airway pressure apparatus such as, for example, the speed of a motor 220 that drives a fan or other air compressive device in the flow generator 20. The sensors 205 may include pressure transducers, air velocity sensors, and humidity sensors that sense the pressure, the velocity, and the humidity of the pressurized air delivered to the user, respectively. The sensors 205 may include current sensors that sense the flow of current into/out of battery 240 or the current delivered to the positive airway pressure apparatus 10 as a whole or to individual parts thereof.

The control unit 26 may be adapted to control the positive airway pressure apparatus 10 in response to signals indicative of the user's physiology received from one or more sensors 205 disposed about the positive airway pressure apparatus 10. The control unit 26 may be adapted to control the positive airway pressure apparatus 10 in response to signals indicative of the operation of the positive airway pressure apparatus 10. For example, sensor(s) 205 may output signals indicative of the speed of the motor 220 that drives the fan or other air compressive device in the flow generator 20, indicative of the pressure of the pressurized air delivered to the user, or indicative of the humidity of the pressurized air delivered to the user.

Accordingly, in order to regulate the positive airway pressure apparatus 10 to deliver the positive pressure therapy to the user, the control unit 26 may be configured to output one or more control signals to various components of the flow generator 20 and other components of the positive airway pressure apparatus 10 and/or otherwise adapted to regulate the positive airway pressure apparatus 10 in response to the signals from the one or more sensors 205. In some exemplary aspects, the control unit 26 may control the pressure of the pressurized air delivered to the user in response to the one or more signals by modulating the speed of the motor 220 that drives a fan or other air compressive device in the flow generator 20. In other exemplary aspects, the control unit 26 may modulate one or more valves including other flow control devices disposed in the flow generator 20 or otherwise disposed throughout the positive airway pressure apparatus 10 in order to regulate the pressure of the pressurized air delivered to the user. In still other exemplary aspects, the control unit 26 may regulate the pressure of the pressurized air delivered to the user in response to the one or more signals by modulating both the speed of a motor 220 that drives a fan or other air compressive device in the flow generator 20 and one or more valves including other flow control devices disposed in the flow generator 20 or otherwise disposed throughout the positive airway pressure apparatus 10. In still other exemplary aspects, the control unit 26 may receive signals from sensor(s) 205 indicative of the humidity of the pressurized air delivered to the user, and, for example, modulate heat generation within the humidifier 250 in order to regulate the humidity of the pressurized air delivered to the user.

The positive airway pressure apparatus 10, as directed by the control unit 26, delivers a positive pressure therapy at a therapeutic pressure $p_T$ to the user, and the therapeutic pressure may vary during the course of the positive pressure therapy. The therapeutic pressure $p_T$, in various aspects, is a prescribed pressure established by a health care professional based upon the user's anatomy, physiology and clinical condition, and may be chosen, for example, as the minimum pressure required for support of the user's airways in order to prevent apneic events. In various aspects, the therapeutic pressure $p_T$ may vary based upon user's breathing as detected by the positive airway pressure apparatus 10 in a prescribed manner.

In various aspects, the positive airway pressure apparatus 10 delivers pressurized air to the user at a base pressure $p_B$ and at a therapeutic pressure $p_T$, and may also deliver pressurized air to the user at one or more pressures intermediate of the base pressure $p_B$ and the therapeutic pressure $p_T$. The base pressure $p_B$, for example, is a non-therapeutic pressure provided at start-up of the positive airway pressure apparatus 10 as the user retires. The base pressure $p_B$ may be initiated before, during, or after the user interface 40 is secured over the user's airways, and is typically a low pressure that the user finds comfortable at the start of the positive pressure therapy. In various aspects, this base pressure $p_B$ and corresponding airflow may provide some initial support to the user's airway. The base pressure $p_B$ should be at least a pressure required to flush exhaled $CO_2$ out of the mask 60 in various aspects.

While the therapeutic pressure $p_T$ and the base pressure $p_B$ may vary from user to user, the $p_T$ is typically at least about 2 cm of $H_2O$ greater than that of the base pressure $p_B$. For example, the therapeutic pressure $p_T$ may range from about 4 cm of $H_2O$ to about 20 cm of $H_2O$, although, for some users, the therapeutic pressure $p_T$ may be as high as about 30 cm of $H_2O$. The base pressure $p_B$, for example, is generally a positive pressure at least sufficient to flush $CO_2$ that may range up to about 6 cm of $H_2O$, but could be greater with certain user interfaces or certain configurations of positive airway pressure apparatus 10.

It should be recognized that the base pressure $p_B$, the therapeutic pressure $p_T$, and pressures intermediate to the base pressure $p_B$ and the therapeutic pressure $p_T$ may have, in various aspects, multiple pressure components, and the positive airway pressure apparatus 10 may adjust between these pressure components in various ways. For example, the therapeutic pressure $p_T$ may include a pressure component generally delivered to the user during inhalation and a pressure component generally delivered to the user during exhalation. Similarly, in various aspects, the base pressure $p_B$ may include a pressure component generally delivered to the user during inhalation and a pressure component generally delivered to the user during exhalation. Other pressures delivered to the user by the positive airway pressure apparatus including pressures intermediate to the base pressure $p_B$ and the therapeutic pressure $p_T$ may also include multiple pressure components, for example, a pressure component generally delivered to the user during inhalation and a pressure component generally delivered to the user during exhalation. Accordingly, in some aspects, sensors 205 detect physiologic responses such as inhalation and exhalation of the user, communicate signals indicative thereof to the control unit 26, and the control unit 26 regulates the positive airway pressure apparatus 10, for example, to deliver a pressure component during inhalation and a pressure component during exhalation.

The battery 240 provides electric power to the positive airway pressure apparatus 10 as a sole or primary source of power or, in certain aspects, as an alternative to mains electric 247 or other outside power sources. In certain aspects, the battery 240 may provide electrical power when mains electric 247 is not convenient or is not available. The battery 240, for example, may serve as a backup source of electrical power in the event of failure of the mains electric 247. The positive airway pressure apparatus 10 may be configured to switch the source of electrical power between mains electric 247 and battery 240, so that, if a power failure occurs in the mains electric 247, the positive airway pressure apparatus 10 automatically switches the source of electric power from mains electric 247 to battery 240. Upon restoration of mains electric power, the positive airway pressure apparatus 10 may automatically switch the source of electrical power from battery 240 to mains electric 247. Accordingly, in various aspects, the battery 240 carries a sufficient maximum battery charge $Q_0$ at battery capacity to sustain at least the delivery of the therapeutic pressure $p_T$ to the user for a generally normal sleep period—from about 5 hours to about 8 hours, for example.

The battery 240 may be formed as, inter alia, an electrolytic cell, fuel cell, or flow cell. The battery 240 may be primary (disposable) or secondary (rechargeable). In aspects wherein the battery 240 is a secondary battery, the battery 240 may be, for example, nickel-cadmium (NiCd), nickel-metal hydride (NiMH), lithium ion, lithium polymer, or lithium-transition metal oxides such at lithium titanate ($Li_4Ti_5O_{12}$). The secondary battery may be recharged from mains electric or other external power source.

The battery 240 is located about the positive airway pressure apparatus 10 to electrically communicate with at least portions of the positive airway pressure apparatus 10. In some aspects, the battery 240 may be integral with the positive airway pressure apparatus 10, for example, by being contained in the flow generator housing 22 to be generally integral with the flow generator 20. In other aspects, the battery 240 is removable from the remainder of the positive airway pressure apparatus 10. For example, the battery 240 is removably slidably received upon the flow generator housing 22 so that the battery 240 may be attached to the flow generator housing 22 or removed from the flow generator housing 22. As used herein, battery 240 further includes a plurality of batteries in series, in parallel, or combinations thereof. The battery 240 may be based in other chemical and/or physical processes and may be located about the positive airway pressure apparatus 10 in other ways, as would be recognized by those of ordinary skill in the art upon review of this disclosure.

One or more sensors 615 are in communication with the battery 240 to detect the battery charge Q stored within the battery 240, the charge entering the battery 240, and/or the charge being drawn from the battery 240 and to communicate signal(s) indicative thereof to the control unit 26 in various aspects. In various aspects the battery 240 may be a smart battery, which is a battery 240 with sensor included therein that provides a signal indicative of the current, voltage, or charge entering and/or being withdrawn from the battery 240 and/or the battery charge Q stored within the battery 240. In other aspects, one or more sensors 615 may be in communication with the battery 240 and/or control unit 26 or data may be otherwise input into the control unit 26 that may measure or otherwise indicate the age of the battery 240, the number of charge/discharge cycles for the battery 240, the storage temperature of the battery 240 or other factors that might effect the batteries 240 ability to hold a charge Q. This data from the sensors 615 or other input source may be integrated into the determination by the control unit 26 of the remaining therapy time $t_R$ that the battery 240 may provide a positive pressure therapy.

In certain aspects, the current leaving the battery 240 may be estimated based on speed of the motor or level of humidity set by the user as measured by sensor 205, for example. The current estimated may be based on look up tables relating current to motor speed or current to humidity settings without the use of sensor 615.

The control unit 26, in various aspects, receives the signal(s) indicative of the current, voltage, or charge entering and/or being withdrawn from the battery 240 and/or battery charge Q within the battery from the sensor(s) 615 and optimizes the operation of the positive airway pressure apparatus 10 to minimize the rate at which the battery charge Q stored within the battery 240 is depleted in order to provide positive pressure therapy to the user throughout the sleep period. In various aspects, for example, the control unit 26 may toggle the I/O interface 270 to use less current by shutting off portions of the I/O interface 270 such as lights and so forth. In various aspects, the control unit 26 may reduce humidification or turn off humidification entirely by reducing or shutting off the current $i_H$ supplied to the humidifier 250. In various aspects, the control unit 26 may switch the positive pressure therapy to a positive pressure therapy that is more conservative of the battery charge Q in the battery 240. For example, the control unit 26 may switch the positive pressure therapy from bi-PAP to CPAP or lower the pressure of the pressurized air delivered to the user to less than the therapeutic pressure $p_T$ but greater than the base pressure $p_B$ in order to deliver at least some level of therapy to the user while reducing the charge being withdrawn from the battery. In various aspects, the control unit 26 tracks the remaining therapy time $t_R$ in the positive pressure therapy, i.e. the time over which positive pressure therapy is targeted to be delivered in order to deliver the positive pressure therapy throughout the desired therapy duration time $t_D$ to the user, and may optimize the operation of the positive airway pressure apparatus 10 in order to deliver positive pressure therapy for remaining therapy time $t_R$. The remaining therapy time $t_R$ is the desired therapy duration time $t_D$ minus the time over which the positive pressure therapy has been delivered prior to the switch to battery 240 as power source in various aspects.

Specific exemplary embodiments of the positive airway pressure apparatus 10 are illustrated in the Figures. FIG. 1A generally illustrates an embodiment of the positive airway pressure apparatus 10. As illustrated in FIG. 1A, the positive airway pressure apparatus 10 includes a flow generator 20, a user interface 40, and a delivery tube 30. The flow generator 20 includes an outlet 24 through which pressurized air generated by the flow generator 20 may pass. The user interface 40 includes an interface conduit 50 and a mask 60. The user interface, as illustrated, also includes various support structures including a mount 48 and support bands 44 to secure the user interface 40 about the user's head and properly position the mask 60 with respect to the user.

The interface conduit 50 has an interface conduit proximal end 52, and interface conduit distal end 54, and defines interface passage 74. The interface conduit distal end 54 is secured to mask 60 such that the interface passage 74 is in fluid communication with a chamber 66 defined by the mask 60. The delivery tube 30 defines a delivery tube passage 36, and the proximal end 32 of the delivery tube 30 may be attached to the outlet 24 of the flow generator 20, as illustrated in FIG. 1A. The distal end 34 of the delivery tube 30 may be secured to the interface conduit proximal end 52 such that pressurized air may be delivered from the outlet 24 of the flow generator 20 through the delivery tube passage 36 and through the interface passage 74 and into the chamber 66 of the mask 60 for inhalation by the user. In the embodiment illustrated in FIG. 1A, the mask 60 is configured to be sealed about the user's nares and to touch the user's face generally proximate the nares.

The flow generator 20, as illustrated in FIG. 1A, includes humidifier 250 formed generally within the lower portion thereof. The humidifier 250 communicates moisture into the pressurized air delivered from the flow generator 20 to the user. The flow generator 20 includes battery 240 generally secured to the flow generator 20 to form the base of the flow generator 20 in the embodiment illustrated in FIG. 1A. In various embodiments, the battery 240 may be engageable/disengageable with the flow generator housing 22 of the flow generator 20.

Figure 1B:
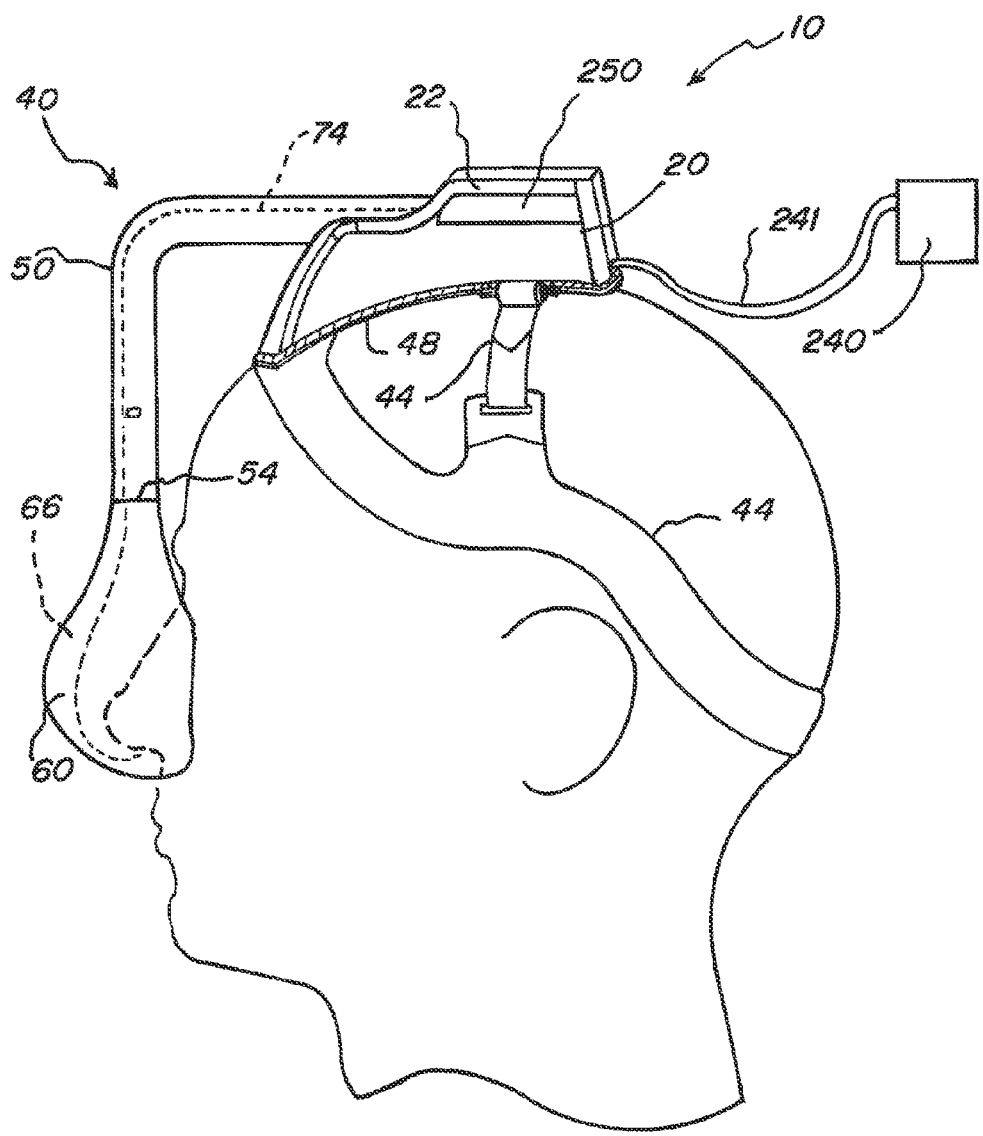
FIG. 1B illustrates by perspective view another implementation of a positive airway pressure apparatus.

Another embodiment of the positive airway pressure apparatus 10 is illustrated in FIG. 1B. The embodiment illustrated in FIG. 1B includes a flow generator 20 that is attached to the user interface 40 generally about the mount 48. The mount 48 provides a generally rigid structure to which portions of the user interface 40 including the flow generator 20, portions of the interface conduit 50, and one or more of the support bands 44 may be secured. A plurality of support bands 44 are provided to secure the user interface 40 including the flow generator 20 about the user's head. Pressurized air may be communicated from the flow generator 20 through interface passage 74 defined by interface conduit 50 to the chamber 66 of mask 60. The mask 60, in this embodiment, may be sealed about the user's nares to deliver pressurized air for inhalation by the user. The interface conduit 50 is shown as extending from the flow generator 20 housing 22 and bending to pass over the user's face without touching the user's face and is generally in a fixed orientation with respect to the user's head including the face or may alternatively use various other configurations currently available for positive airway pressure therapy devices as will be recognized by those skilled in the art upon review of the present disclosure.

The flow generator 20, as illustrated in FIG. 1B, includes humidifier 250 formed generally within the upper portion thereof to communicate moisture into the pressurized air delivered from the flow generator 20 to the user. The flow generator 20 includes battery 240 disposed remotely from the flow generator 20 in the embodiment illustrated in FIG. 1B. In this embodiment, the battery 240 communicates with the remainder of the positive airway pressure apparatus 10 via wire 241.

Figure 2:
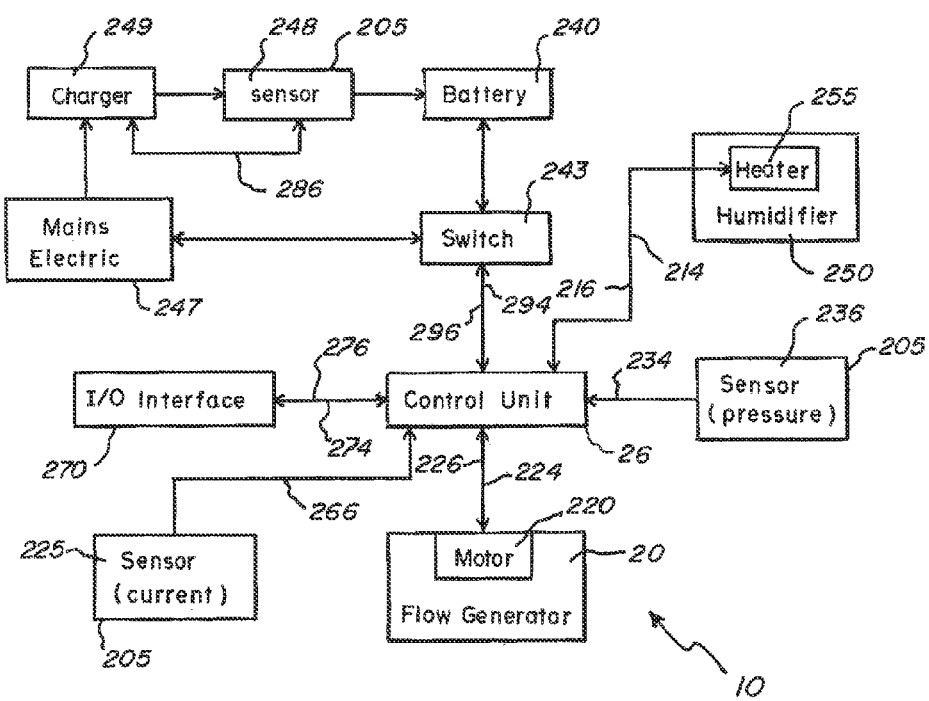
FIG. 2 illustrates by block diagram portions of an implementation of a positive airway pressure therapy apparatus.

FIG. 2 illustrates an exemplary embodiment of the control unit 26 in the positive airway pressure apparatus 10. The positive airway pressure apparatus 10, as illustrated in FIG. 2, includes I/O interface 270, flow generator 20 with motor 220, and humidifier 250 with heater 255 all in communication with the control unit 26. As illustrated in FIG. 2, the control unit 26 receives signal 276 from the I/O interface 270, which communicates information from the I/O interface 270 to regulate the operation of the positive airway pressure apparatus 10. The control unit 26 communicates control signal 274 to the I/O interface 270, and the control signal 274 alters the I/O interface 270 in ways indicative of the operation of the positive airway pressure apparatus 10.

As illustrated, a sensor 236 may detect the pressure of the pressurized air delivered to the user and may communicate a signal 234 indicative thereof to the control unit 26. The control unit 26 may communicate with motor 220 including sensors 205 secured thereto (not shown) via signal 226 and control signal 224 to at least one of ascertain the rotational speed of the motor 220 and to control the rotational speed of the motor 220, respectively, in order to control the pressure of the pressurized air delivered to the user.

The heater 255 may communicate a signal 216 indicative of the operation of the heater 255 to the control unit 26. The control unit 26 may then utilize a signal 216 to formulate a control signal 214 which can then be communicated to the heater 255 within the humidifier 250 to control the humidity delivered to the user. The signal 216, for example, may be indicative of the humidity of the pressurized air delivered to the user. The control signal 214, for example, may alter the heater current $i_H$ delivered to the heater 255 by pulse width modulation. In this implementation, the control unit 26 may modulate the pulse width $t_{pw}$ of the heater current $i_H$ in increments/decrements of $\Delta t_H$ but may modulate the pulse width $t_{pw}$ of the heater current $i_H$ in other ways or otherwise modulate the heater current $i_H$ in other embodiments.

Current sensor(s) 275 may be disposed about the positive airway pressure apparatus 10 to detect the heater current $i_H$ delivered to heater 255, the motor current $i_m$ delivered to the motor 220, and the other current $i_o$ delivered to other portions of the positive airway pressure apparatus 10, and current sensor(s) 275 communicate signal(s) 266 indicative thereof to control unit 26 in this implementation. Sensor 248 may interact with charger 249 via path 286 to detect whether or not current is available from mains electric 247 and to control the charging of the battery 240. When current is available from mains electric 247, the current may pass through charger 249 to battery 240. Upon detecting a loss of current from mains electric 247, the control unit 26 may activate switch 243 using a control signal 294 to switch the positive airway pressure apparatus 10 to battery operation, and the control unit 26 optimizes the operation of the positive airway pressure apparatus 10 via execution of control algorithm 501 illustrated in FIG. 3A in order to deliver positive pressure therapy for remaining therapy time $t_R$. Signal 296 from the switch 243 may confirm the status of the switch 243 in this embodiment. Upon detecting the availability of mains electric 247, the control unit 26 may activate switch 243 using a control signal 294 or otherwise to switch the positive airway pressure apparatus 10 to mains electric operation.

Figure 3A:
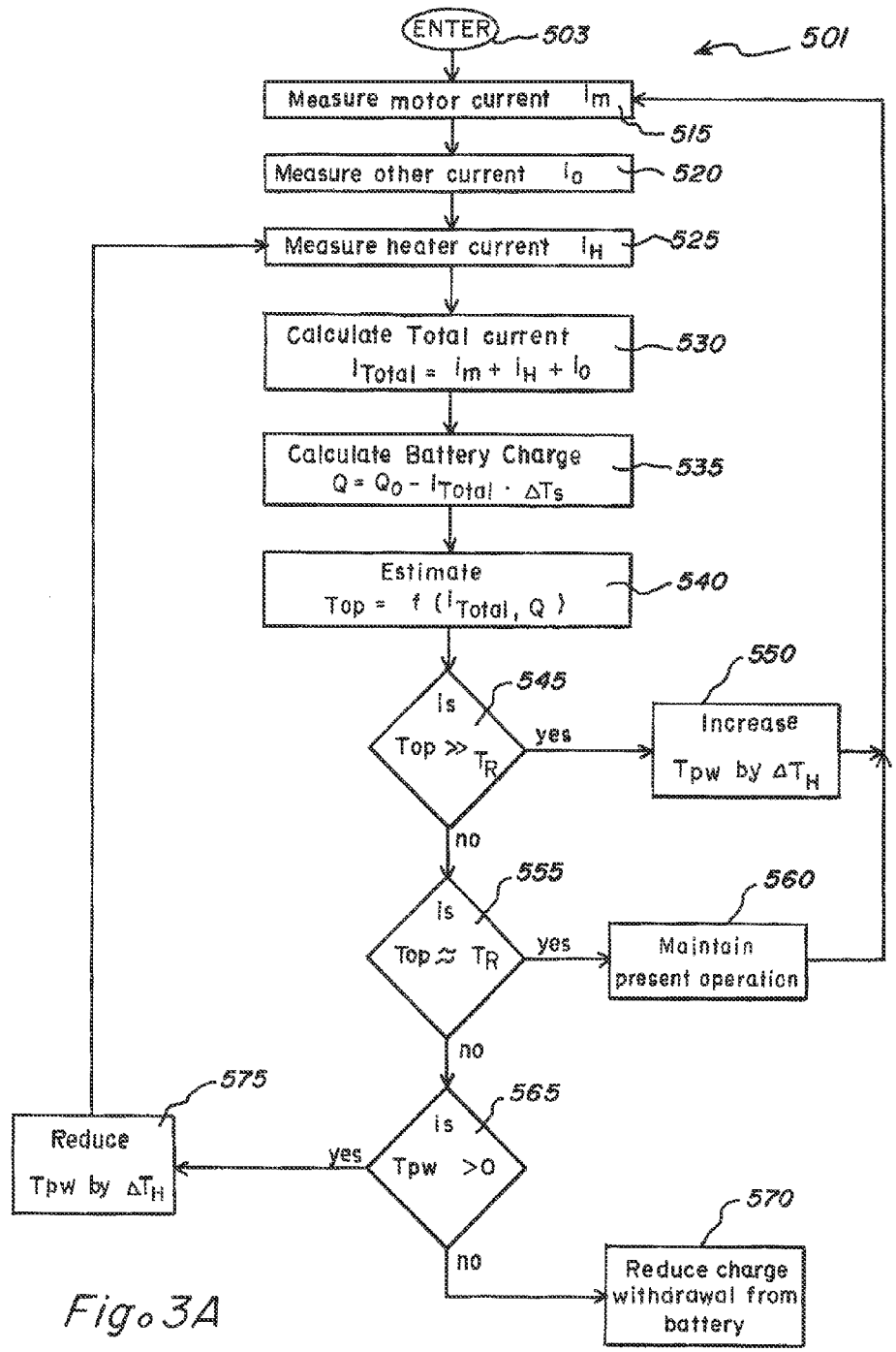
FIG. 3A illustrates by flow chart a portion of the operation of the implementation of the positive airway pressure apparatus of FIG. 2.

As directed by control algorithm 501 illustrated in FIG. 3A, the control unit 26 minimizes the rate at which the battery charge Q stored within the battery 240 is depleted by reducing the level of humidification in order to provide positive pressure therapy for the remaining therapy time $t_R$. Some humidification may be provided during the remaining therapy time $t_R$ by the positive airway pressure apparatus 10 as directed by control algorithm 501. In this embodiment, the battery charge Q of the battery 240 is assumed to be maximum battery charge $Q_0$ initially, and the desired therapy duration time $t_D$ is fixed at a preset value in this implementation of control algorithm 501.

The control algorithm 501 is entered at step 503. The motor current $i_m$ delivered to the motor 220 is measured at step 515, the heater current $i_H$ delivered to the heater 255 is measured at step 525, and other current $i_o$ used by other portions of the positive airway pressure apparatus 10 such as, for example, the I/O interface 270 is determined at step 520, and the control unit 26 may query one or more current sensors 275 to implement steps 515, 520, 525. At step 530, the total current draw $i_{Total} = i_m + i_H + i_o$ is calculated. The battery charge Q of battery 240 is estimated as the maximum battery charge $Q_0$ less the total current $i_{Total}$ withdrawn from battery 240 over time $\Delta t_s$ at step 535 where $\Delta t_s$ is indicative of the time over which the positive airway pressure apparatus 10 has drawn total current $i_{Total}$ from battery 240. A clock, counter, or similar feature is provided as part of the control unit 26 to determine $\Delta t_s$ in this embodiment, and the control algorithm 501 may be executed at intervals of $\Delta t_s$. The remaining battery operational time $t_{op}$ for which the positive airway pressure apparatus 10 may be operated on battery power is calculated as a function $f$ of the battery charge Q and the total current draw $i_{Total}$ at step 540 per equation 1.

$$t_{op} = f(i_{Total}, Q_0) \quad (1)$$

The function $f$ in equation 1 may be based on Peukert's equation and the characteristics of battery 240 in various implementations.

If, at step 545, the remaining battery operational time $t_{op}$ is sufficiently greater than the remaining therapy time $t_R$, the battery charge Q in the battery 240 may allow for increase in humidity and the pulse width $t_{pw}$ delivered to the heater 255 may be increased by $\Delta t_H$ at step 550, if desired.

If the remaining battery operational time $t_{op}$ is generally equal to the remaining therapy time $t_R$, per step 555, the battery charge Q is sufficient to maintain the present operation of the positive airway pressure apparatus 10, and the control algorithm 501 proceeds from step 555 to step 560. No adjustment is made to the operation of the heater 255 in the humidifier 250—the present operation of the positive airway pressure apparatus 10 is maintained. The control algorithm 501 may be re-executed after some time increment $\Delta t_s$ from step 550 or step 555 by the control unit 26 to determine if adjustment of the operation of the positive airway pressure apparatus 10 is necessary, and the remaining therapy time $t_R$ may be decremented by $\Delta t_s$.

If the remaining battery operational time $t_{op}$ is less than the remaining therapy time $t_R$, the battery charge Q in the battery 240 is insufficient to maintain the present operation of the positive airway pressure apparatus 10, and the control algorithm 501 proceeds from step 555 to step 565 to reduce the rate of withdrawal of charge from the battery 240.

At step 565, if the pulse width $t_{pw}$ is zero, the heater 255 is off, and the control algorithm 501 proceeds to step 570 where control may pass to other algorithms adapted to reduce the rate of withdrawal of charge from the battery 240 by, for example, reduction of the pressure of the pressurized air delivered to the user. At step 565, if the pulse width $t_{pw}$ is non-zero, the algorithm 501 proceeds to step 575, which decrements the pulse width $t_{pw}$ delivered to the heater 255 by $\Delta t_H$. Algorithm 501 loops from step 575 back to step 525 to determine if further reduction of the pulse width $t_{pw}$ of the heater current $i_H$ is necessary in order to reduce the rate of withdrawal of charge from the battery 240 to provide positive pressure therapy for the remaining therapy time $t_R$.

Figure 3B:
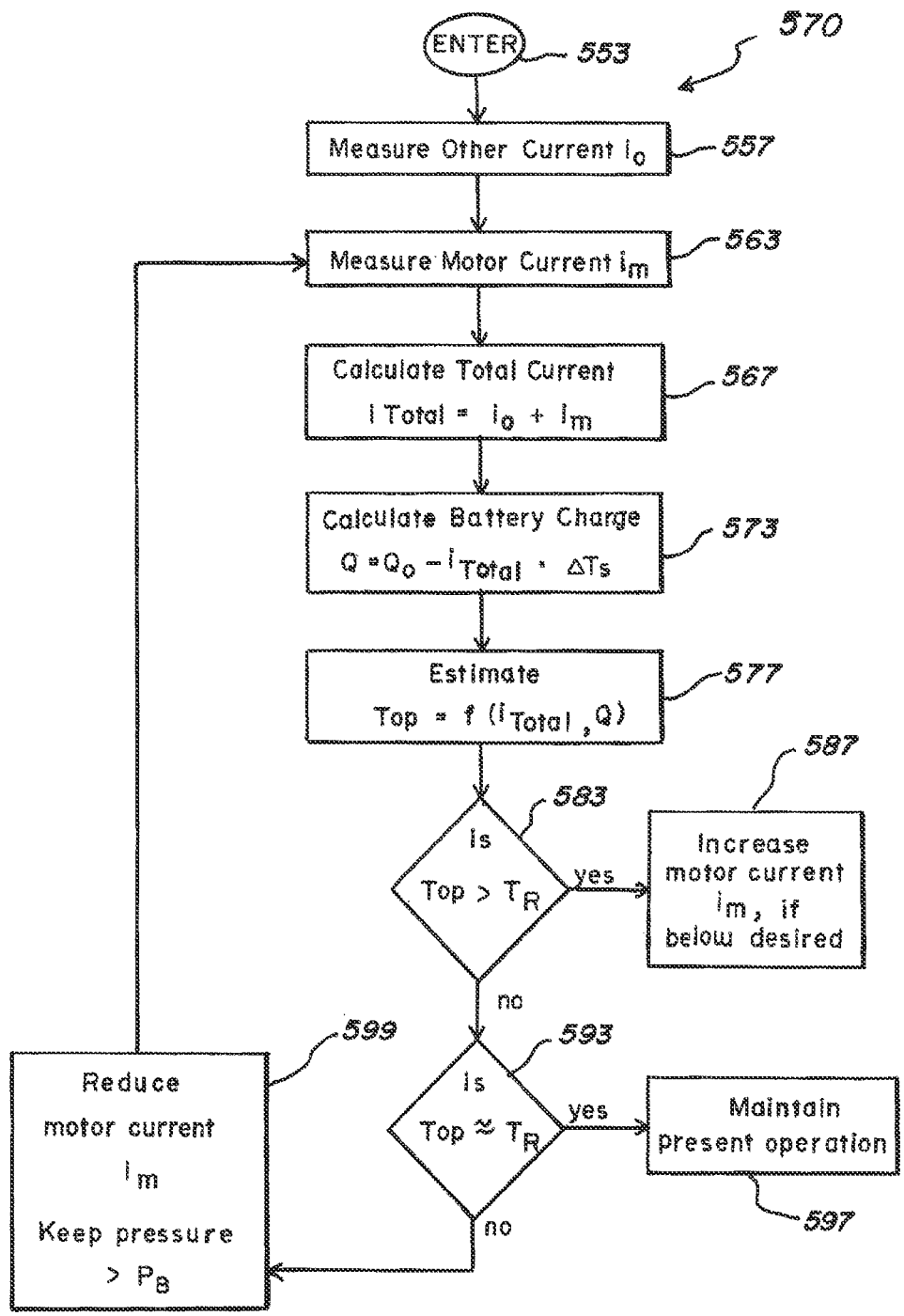
FIG. 3B illustrates by flow chart further portions of the operation of the implementation of the positive airway pressure apparatus of FIG. 2.

FIG. 3B illustrates an exemplary control algorithm corresponding to step 570 wherein step 570 is broken into substeps. The motor current $i_m$ delivered to the motor 220 and, hence, the pressure of the pressurized air delivered to the user is reduced by the control algorithm illustrated in FIG. 3B in order to provide positive pressure therapy for the remaining therapy time $t_R$. Step 570 is entered at step 553, as illustrated in FIG. 3B. The other current $i_o$ delivered to other portions of the positive airway pressure apparatus 10 is measured at step 557, and the motor current $i_m$ delivered to the motor 220 is measured at step 563. Note that the heater current $i_H$ delivered to the heater 255 is zero. The total current draw $i_{Total}=i_m+i_o$ is calculated at step 567 and the battery charge Q is calculated at step 573 by subtracting the current withdrawn from the battery over a previous time period 240 from the charge $Q_0$. The remaining battery operational time $t_{op}$ for which the positive airway pressure apparatus 10 may be operated is calculated as a function $f$ of the battery charge Q and the total current draw $i_{Total}=i_m+i_o$ over the previous time period at step 577.

$$t_{op}=f(i_{Total},Q_0) \quad (2)$$

If at step 583, the remaining battery operational time $t_{op}$ is greater than the remaining therapy time $t_R$, the battery charge Q in the battery 240 may be sufficient to allow for an increase in the motor current $i_m$ if this is below the desired level at step 587. If, at step 593, the operational time $t_{op}$ is generally equal to the remaining therapy time $t_R$, the battery charge Q in the battery 240 is sufficient to maintain the present operation of the positive airway pressure apparatus 10, and the branch is from step 593 to step 597 which maintains present operation. If, per step 593, the remaining battery operational time $t_{op}$ is less than the remaining therapy time $t_R$, the battery charge Q in the battery 240 is insufficient to maintain the present operation of the positive airway pressure apparatus 10, and the branch is from step 593 to step 599 which reduces the motor current $i_m$ delivered to the motor 220 in order to decrease the rate of withdrawal of charge from the battery 240 by the motor 220. Hence, the pressure of the pressurized air delivered to the user is decreased. Motor current $i_m$ delivered to the motor 220 may be reduced by pulse width modulation or in other ways as would be recognized by those of ordinary skill in the art upon study of this disclosure. In some embodiments, the motor current $i_m$ is reduced, if necessary, until the pressure delivered to the user is generally equal to the base pressure $p_B$. The pressure delivered to the user is not allowed to drop below the base pressure $p_B$ in order maintain flushing exhaled $CO_2$ out of the mask 60, in various aspects. If the at any time the control unit 26 determines that battery charge Q is insufficient to maintain the base pressure $p_B$ required to flush exhaled $CO_2$ out of the mask 60, a signal may be sent from the control unit to an alarm configured to alert a user of the potentially dangerous condition prior to or at inception of the insufficient base pressure $p_B$ condition.

In the exemplary embodiment of FIGS. 2, 3A, and 3B, the control unit 26 executes algorithm 501 upon switching from mains electric 247 to battery 240 as the source of power. The control unit 26 may execute algorithm 501 or portions thereof periodically thereafter in order to maintain the remaining battery operational time $t_{op}$ greater than the remaining therapy time $t_R$. The control unit 26 may execute control algorithm 501 following changes in therapeutic pressure $p_T$ or other changes in the operation of the positive airway pressure apparatus 10 in order to maintain the operational period $t_{op}$ greater than the remaining therapy time $t_R$. It is assumed in this implementation that the battery 240 has the maximum battery charge $Q_0$ at the start of battery operation of the positive airway pressure apparatus 10 and the battery charge Q is estimated periodically thereafter by deducting the current withdrawn from the battery as determined by current sensors 275 located about the positive airway pressure apparatus 10.

Figure 4:
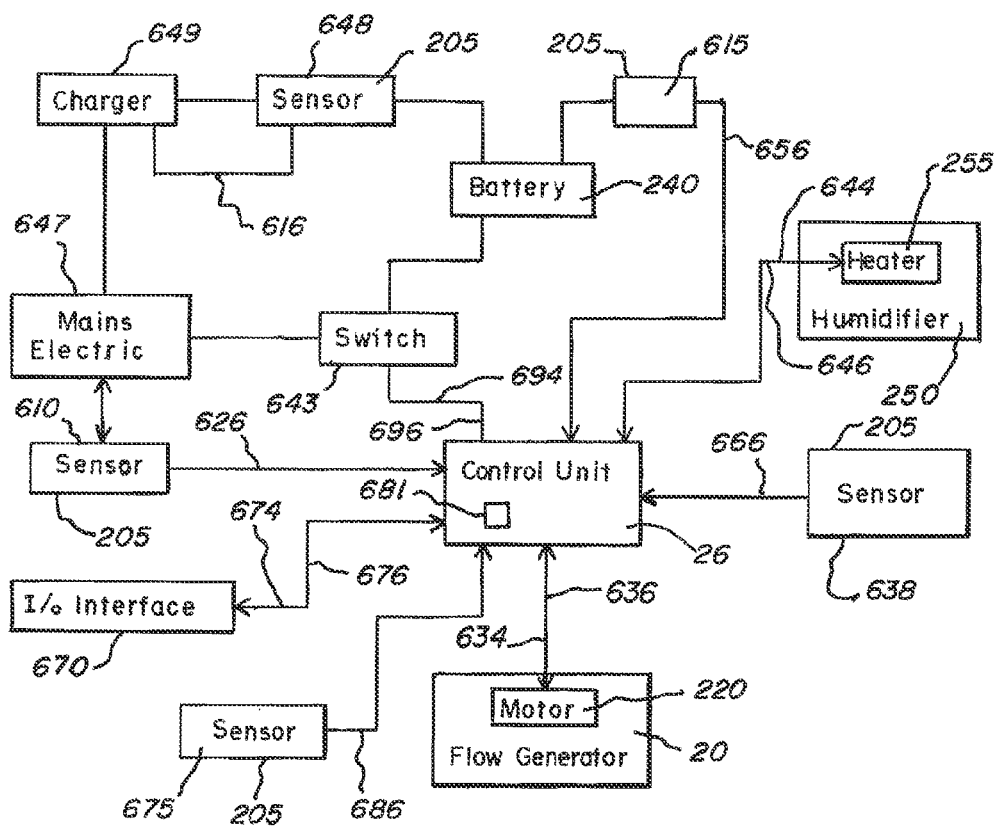
FIG. 4 illustrates by block diagram portions of an implementation of a positive airway pressure apparatus.
Figure 5:
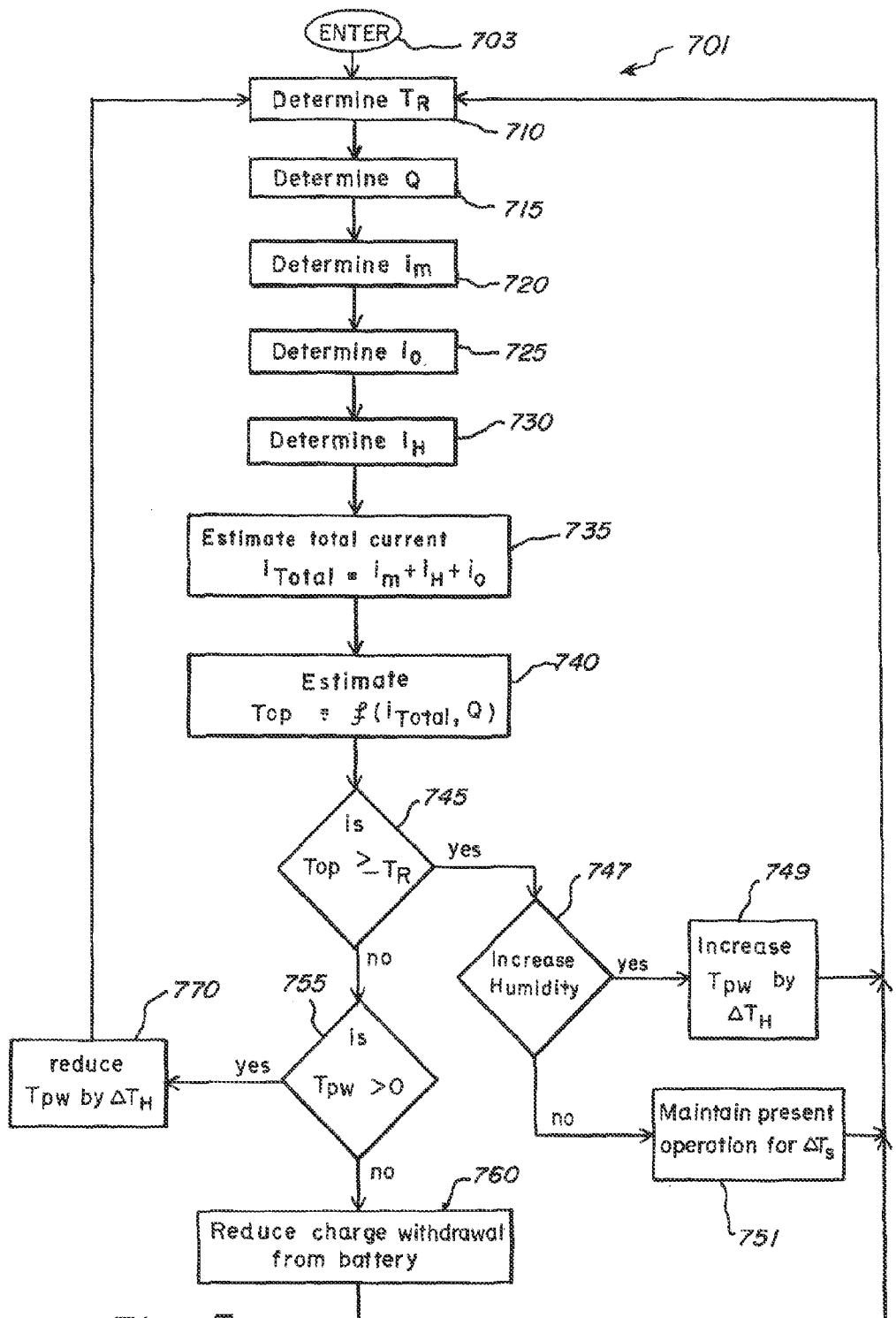
FIG. 5 illustrates by flow chart a portion of the operation of the implementation of the positive airway pressure apparatus of FIG. 4.

Another exemplary embodiment of the control unit 26 in the positive airway pressure apparatus 10 and corresponding control algorithm 701 are illustrated in FIG. 4 and in FIG. 5, respectively. The implementation of FIGS. 4 and 5 allows the positive airway pressure apparatus 10 to respond to repeated failures of mains electric 647, to respond to the state of the battery charge Q within the battery 240, and to respond to decreases in the remaining therapy time $t_R$ as the time for which the positive pressure therapy has been delivered progresses toward the desired therapy duration time $t_D$. In the implementation illustrated in FIGS. 4 and 5, the battery charge Q may be less than the maximum battery charge $Q_0$. In order to determine the battery charge Q, the charging current and discharging current may be monitored using a coulomb counter such as, for example, a device marketed by Texas Instruments, Inc., a corporation headquartered in Dallas, Tex., as model BQ26229 in some implementations. The charging and discharging current may also be monitored using impedance of the battery with a component such as, for example, a device marketed by Texas Instruments, Inc., a corporation headquartered in Dallas, Tex., as model BQ20275. Other sensor(s) as would be recognized by those of ordinary skill in the art upon study of this disclosure may be employed to track battery charge Q in various other implementations.

The positive airway pressure apparatus 10, as illustrated in FIG. 4, includes I/O interface 670, flow generator 20 with motor 220, and humidifier 250 with heater 255 all in communication with the control unit 26. As illustrated in FIG. 4, the control unit 26 receives signal 676 from the I/O interface 670, which communicates information form the I/O interface 670 to regulate the operation of the positive airway pressure apparatus 10. For example, the user may regulate the therapeutic pressure $p_T$, the base pressure $p_B$, the time required to ramp up to the therapeutic pressure $p_T$ from the base pressure $p_B$ via the I/O interface 670. The user, in this implementation, may regulate the desired therapy duration time $t_D$ using the I/O interface 670. In other implementations, usage of the positive airway pressure apparatus 10 is monitored, and the desired therapy duration time $t_D$ is determined therefrom.

The control unit 26 communicates control signal 674 to the I/O interface 670 to alter the I/O interface 670 in ways indicative of the operation of the positive airway pressure apparatus 10 in this implementation. For example, the control unit 26 may cause the I/O interface 670 to indicate the desired therapy duration time $t_D$, the therapeutic pressure $p_T$, and so forth.

As illustrated, sensor 638 detects the pressure of the pressurized air delivered to the user and communicates signal 666 indicative thereof to control unit 26. The control unit 26 communicates with motor 220 including sensors secured thereto via signal 636 and control signal 634 to ascertain the rotational speed of the motor 220 and to control the rotational speed of the motor 220, respectively, in order to control the pressure of the pressurized air delivered to the user.

The heater 255 within humidifier 250 communicates signal 646 indicative of the operation of the heater 255 to the control unit 26. The control unit 26 then utilizes signal 646 to formulate a control signal 644 which is then communicated to the heater 255 within the humidifier 250 to control the humidity delivered to the user. Signal 646, for example, may be indicative of the humidity of the pressurized air delivered to the user. The control signal 644, for example, may alter the heater current $i_H$ delivered to the heater 255 by pulse width modulation. In this example, the control unit 26 modulates the pulse width $t_{pw}$ of the heater current $i_H$ in increments/decrements of $\Delta t_H$ but may modulate the pulse width $t_{pw}$ of the heater current $i_H$ in other ways or otherwise modulate the heater current $i_H$ in other embodiments.

Current sensor(s) 675 are disposed about the positive airway pressure apparatus 10 to detect the heater current $i_H$ delivered to heater 255, the motor current $i_m$ delivered to the motor 220, and the other current $i_o$ delivered to other portions of the positive airway pressure apparatus 10, and current sensor(s) 675 communicate signal(s) 676 indicative thereof to control unit 26 in this implementation.

The control unit 26, in this implementation, receives signal 626 from sensor 610, which detects whether or not current is available from mains electric 647. Upon detecting a loss of current from mains electric 647 via sensor 610, the control unit 26 may activate switch 643 via control signal 694 to switch the positive airway pressure apparatus 10 to battery operation, and the control unit 26 optimizes the operation of the positive airway pressure apparatus 10 via execution of control algorithm 701 illustrated in FIG. 5 in order to deliver positive pressure therapy for remaining therapy time $t_R$. Signal 696 from the switch 643 confirms the status of the switch 643 in this embodiment. Upon detecting that current is available from mains electric 647 via sensor 610, the control unit 26 may activate switch 643 via control signal 694 to switch the positive airway pressure apparatus 10 from battery operation to operation from mains electric 643 and may supply current from mains electric 643 to the battery 240 to recharge the battery 240 when the battery charge Q of the battery 240 is less than the capacity. The current passes from mains electric 647 through charger 649 to the battery 240 in this implementation. Sensor 648 interacts with charger 649 via path 616 to detects whether or not current is available from mains electric 247 and to control the charging of the battery 240.

In the embodiment of FIG. 4, sensor 615 is provided to detect the battery charge Q of the battery 240, which varies as charge is supplied to or withdrawn from the battery 240. The battery 240 may be a smart battery or otherwise adapted to include the sensor 215 in various implementations, and the sensor 615 is a coulomb counter in this implementation. In other implementations, the sensor 615 may be a voltage detector, current detector, impedance tracking detector or other sensor/detector that may track the flow of current into and/or out of the battery 240 or otherwise produce data usable to establish the charge in a battery 240. Signal 656 from the sensor 615 indicates the battery charge Q to the control unit 26 as illustrated.

The control unit 26 in this implementation includes a clock 681 that tracks the time that the positive pressure therapy has been delivered to the user among other times and timing functions in accordance with the present inventions. The remaining therapy time $t_R$ is the desired therapy duration time $t_D$ minus the time that the positive pressure therapy has been delivered to the user.

As directed by control algorithm 701, the control unit 26 minimizes the depletion rate of the battery charge Q stored within the battery 240 by reducing humidification in order to provide positive pressure therapy for the remaining therapy time $t_R$.

The control algorithm 701 is entered at step 703. The remaining therapy time $t_R$ is calculated as the desired therapy duration time $t_D$ minus the time that the positive pressure therapy has been delivered to the user at step 710 as determined by clock 681. The battery charge Q stored within the battery 240 is determined at step 715 through query of sensor 616 by the control unit 26. The motor current $i_m$ delivered to the motor is measured at step 720, the heater current $i_H$ delivered to the heater is measured at step 730, and other current $i_o$ used by other portions of the positive airway pressure apparatus 10 such as, for example, the I/O interface 670 is measured at step 725, and the control unit 26 may query one or more current sensors 675 to implement steps 720, 725, 730. At step 735, the total current draw $i_{Total} = i_m + i_H + i_o$ is calculated.

The remaining battery operational time $t_{op}$ for which the positive airway pressure apparatus 10 may be operated on battery is calculated as a function $f$ of the battery charge Q of battery 240 as determined from sensor 615 and the total current draw $i_{Total} = i_m + i_H + i_o$ at step 740.

$$t_{op} = f(i_{Total}, Q) \quad (3)$$

The function $f$ may be based on, for example, Peukert's equation and the characteristics of battery 240 in various implementations.

If the desired therapy operational time $t_{op}$ is greater than or generally equal to the remaining therapy time $t_R$, an increase in humidity may be allowable. The control algorithm 701 passes from step 745 to step 747, and at step 747 checks to determine if an increase in humidity is needed, and if sufficient battery charge Q is available to increase the humidity. If so, the control algorithm 701 passes from step 747 to step 749 designed to allow an increment of the pulse width $t_{pw}$ by $\Delta t_H$ and thereby increase the humidity of the pressurized air delivered to the user. Otherwise, the control algorithm passes from step 747 to step 751. At step 751, no adjustment is made to the operation of the heater 255—the present operation of the positive airway pressure apparatus 10 is maintained as sufficient battery charge Q remains in the battery 240 to maintain the present operation of the positive airway pressure apparatus 10 and/or there is no need for increased humidity. The control algorithm 701 may loop back to step 710 after some time increment $\Delta t_s$ from either step 749 or step 751 to determine if adjustment of the operation of the positive airway pressure apparatus 10 is necessary at that later time.

If, per step 745, the desired therapy operational time $t_{op}$ is less than the remaining therapy time $t_R$, insufficient battery charge Q remains in the battery 240 to maintain the present operation of the positive airway pressure apparatus 10, and the control algorithm 701 proceeds from step 745 to step 755 to reduce the rate of charge withdrawal from the battery 240.

At step 755, if the pulse width $t_{pw}$ is zero, the heater 255 is off, and the algorithm 701 proceeds to step 760 where control may pass to other algorithm(s) adapted to reduce the rate of charge withdrawal from the battery 240 in order to provide positive pressure therapy for the remaining therapy time $t_R$. The algorithm(s) implemented at step 760 could reduce the motor current $i_m$ delivered to the motor 220 and, hence, the pressure of the pressurized air delivered to the user in order to provide positive pressure therapy for the remaining therapy time $t_R$. The pulse width of the motor current $i_m$ delivered to the motor 220 is reduced or the motor current $i_m$ delivered to the motor 220 is otherwise modulated to alter the motor current $i_m$ delivered to the motor 220 at step 760 in various implementations of step 760, for example, by extension of the algorithm illustrated in FIG. 3B. The motor current $i_m$ delivered to the motor 220 could be increased as well as decreased, in various implementations, dependent upon the battery charge Q of battery 240.

At step 755, if the pulse width $t_{pw}$ is non-zero, the algorithm 701 proceeds to step 770, which decrements the pulse width $t_{pw}$ by $\Delta t_H$. Algorithm 701 then loops back from step 770 to step 710 to determine if further reduction of the pulse width $t_{pw}$ delivered to the heater $i_H$ is necessary in order to provide positive pressure therapy for the remaining therapy time $t_R$.

In the exemplary embodiment of FIGS. 4 and 5, the control unit 26 executes algorithm 701 upon switching from mains electric to battery 240. The control unit 26 may execute algorithm 701 periodically thereafter in order to maintain the operational period $t_{op}$ generally equivalent to the remaining therapy time $t_R$, in order to optimize the delivery of positive airway pressure therapy to the user. The control unit 26 may execute control algorithm 701 following changes in therapeutic pressure $p_T$ or other changes in the operation of the positive airway pressure apparatus 10 in order to maintain the desired therapy operational time $t_{op}$, greater than or equal to the remaining therapy time $t_R$. If the at any time the control unit 26 determines that battery charge Q is insufficient to maintain the base pressure $p_B$ required to flush exhaled $CO_2$ out of the mask 60, a signal may be sent from the control unit to an alarm configured to alert a user of the potentially dangerous condition prior to or at inception of the insufficient base pressure $p_B$ condition.

Methods are disclosed herein to provide positive pressure therapy to the user using a positive airway pressure apparatus 10 operating under power provided by battery 240. The methods may include delivering a positive pressure therapy to a user using the positive airway pressure apparatus 10, and delivering the positive airway pressure therapy generally only when the user is sleeping including the times during which the user has retired in an attempt to sleep. In various aspects, the methods may include switching the power source of the positive airway pressure apparatus 10 from mains electric 247, 647 to battery 240, determining the total current $i_{Total}$ drawn from the battery 240 by the positive airway pressure apparatus 10 while delivering the positive pressure therapy, determining the remaining therapy time $t_R$ over which the positive pressure therapy is to be delivered to the user, and reducing current $i_{total}$ drawn from the battery 240 thereby allowing the delivery of positive pressure therapy to the user for the remaining therapy time $t_R$. The methods, in various aspects, include reducing the humidity of the pressurized air delivered to the user thereby reducing the rate of withdrawal of charge from the battery 240 in order to preserve the battery charge Q of the battery 240. The methods may include reducing the humidity by reducing the current supplied to the humidifier 250, for example, by reducing the heater current $i_H$ supplied to the heater disposed about the humidifier 250 in order to preserve the battery charge Q. Some implementations include reducing water flow within the humidifier 250 thereby reducing current used by pumps and suchlike as well as other flow control mechanisms and heating elements or similar in order to preserve the battery charge Q. Some implementations include reducing water flow to vaporizing element within the humidifier 250 in order to preserve the battery charge Q. The methods, in various aspects, may include reducing therapy pressure by reducing the motor current $i_m$ supplied to the motor within the flow generator in order to preserve the battery charge Q. The methods, in various aspects, include reducing other current $i_o$ drawn by the positive airway pressure apparatus 10 in order to preserve the battery charge Q. In some aspects, the heater current $i_H$, the motor current $i_m$, and/or other current $i_o$ may be increased upon determining that sufficient battery charge Q in the battery 240 is available to support delivering positive pressure therapy to the user for the remaining therapy time $t_R$. The methods, in various aspects, may include altering the pulse width $t_{pw}$ of the current $i_H$ provided to the heater 255 disposed about the humidifier and, in various aspects, include incrementing/decrementing the pulse width $t_{pw}$ in steps of $\Delta t_H$. In some aspects, the methods assume a fixed value for the desired therapy duration time $t_D$. In some aspects, the methods assume that the battery 240 is fully charged at maximum charge $Q_0$. In some aspects, the remaining therapy time $t_R$ is decremented as the positive pressure therapy is delivered. The methods, in various aspects, may include inputting the desired therapy duration time $t_D$ into the respiratory therapy apparatus 10, tracking the time that the positive pressure therapy has been delivered to the user, and calculating the remaining therapy time $t_R$ as the desired therapy duration time $t_D$ minus the time that the positive pressure therapy has been delivered to the user. The methods may include determining the desired therapy duration time $t_D$ based upon prior usage of the positive airway pressure apparatus 10. The methods, in various aspects, include detecting the battery charge Q of the battery 240, and include altering the operation of the positive airway pressure apparatus 10 as the battery charge Q changes and/or the remaining therapy time $t_R$ changes in order to deliver positive pressure therapy to the user for the remaining therapy time $t_R$ with the battery 240 as power source. The methods may include detecting failure of mains electric 247, 647, and may include switching the power source of the positive airway pressure apparatus 10 to battery 240 from mains electric 247, 647 upon detecting failure of mains electric 247, 647. The methods may include switching the power source of the positive airway pressure apparatus 10 from battery 240 to mains electric 247, 647 upon detecting availability of mains electric 247, 647, and may include recharging the battery 240 from the mains electric 247, 647.

The foregoing discussion discloses and describes merely exemplary embodiments. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. A method for operating a positive airway pressure apparatus, comprising:
    determining a therapy time for a positive airway pressure therapy;
    providing a current from a battery to power the positive airway pressure apparatus, including operation of a flow generator of the positive airway pressure apparatus, the flow generator being configured to provide pressurized air for the positive airway pressure therapy to a user interface of the positive airway pressure apparatus;
    determining current drawn from the battery during an elapsed portion of the therapy time;
    estimating, via a control unit, a remaining battery operational time that the current drawn from the battery can power the positive airway pressure apparatus to deliver the positive airway pressure therapy before a charge in the battery is depleted;

comparing the remaining battery operation time with an amount of the therapy time remaining after the elapsed portion; and altering the operation of the positive airway pressure apparatus to modify current flow from the battery, wherein delivery of the positive pressure therapy is maintained throughout the therapy time.

2. The method, as in claim 1, wherein the altering step comprises modifying a current delivered to a humidifier of the positive airway pressure apparatus.

3. The method, as in claim 2, further comprising modifying the current delivered to the humidifier is modifying the current delivered to a heater in the humidifier.

4. The method, as in claim 3, further comprising modifying a pulse width of the current supplied to the heater.

5. The method, as in claim 1, wherein the step of modifying the current includes modifying the current in at least one step.

6. The method, as in claim 1, further providing setting the desired therapy duration time as a fixed value.

7. The method, as in claim 1, the step of determining a remaining therapy time over which a positive pressure therapy is delivered to a user by the positive airway pressure apparatus, further comprising:

inputting a desired therapy duration time into the positive airway pressure apparatus;

tracking the time that the positive pressure therapy has been delivered; and calculating the remaining therapy time as the desired therapy duration time minus the time that the positive pressure therapy has been delivered.

8. The method, as in claim 1, wherein the step of determining a remaining therapy time over which a positive pressure therapy is delivered by the positive airway pressure apparatus includes:

determining a desired therapy duration time from the history of use of the positive airway pressure apparatus;

tracking the time that the positive pressure therapy has been delivered to the user; and calculating the remaining therapy time as the desired therapy duration time minus the time that the positive pressure therapy has been delivered.

* * * * *

UNITED STATES PATENT AND TRADEMARK OFFICE
CERTIFICATE OF CORRECTION

PATENT NO.          : 8,567,397 B2
APPLICATION NO.     : 12/496967
DATED               : October 29, 2013
INVENTOR(S)         : Bruce R. Bowman et al.

Page 1 of 1

It is certified that error appears in the above-identified patent and that said Letters Patent is hereby corrected as shown below:

In the Specification

Column 3 – Line 29
Delete "used" and insert -- used, --

Column 6 – Line 19
Delete "$t_o$" and insert -- $t_D$ --

Column 6 – Line 23
Delete "$I_D$" and insert -- $t_D$ --

Column 12 – Line 17
Delete "$i_H$/" and insert -- $i_H$ --

Column 12 – Line 37
Delete "$t_{op}=f(i_{Total}, Q_o)$" and insert -- $t_{op}=f(i_{Total}, Q)$ --

Column 13 – Line 31
Delete "$t_{op}=f(i_{Total}, Q_o)$" and insert -- $t_{op}=f(i_{Total}, Q)$ --

Column 15 – Line 14
Delete "$t_{pw}$," and insert -- $t_{pw}$ --

Column 17 – Line 8
Delete "$t_{pw}$," and insert -- $t_{pw}$ --

Column 18 – Line 9
Delete "$t_{pw}$," and insert -- $t_{pw}$ --

Signed and Sealed this
Second Day of December, 2014

Michelle K. Lee
*Deputy Director of the United States Patent and Trademark Office*